(12) United States Patent
Park et al.

(10) Patent No.: US 11,854,197 B2
(45) Date of Patent: Dec. 26, 2023

(54) CLASSIFICATION OF MEDICAL IMAGES USING MACHINE LEARNING TO ACCOUNT FOR BODY ORIENTATION

(71) Applicant: Merative US L.P., Ann Arbor, MI (US)

(72) Inventors: Sun Young Park, San Diego, CA (US); Dustin Michael Sargent, San Diego, CA (US)

(73) Assignee: MERATIVE US L.P., Ann Arbor, MI (US)

( * ) Notice: Subject to any disclaimer, the term of this patent is extended or adjusted under 35 U.S.C. 154(b) by 131 days.

(21) Appl. No.: 17/522,196

(22) Filed: Nov. 9, 2021

(65) Prior Publication Data
US 2023/0146953 A1  May 11, 2023

(51) Int. Cl.
*G06T 7/00* (2017.01)
*G06T 7/70* (2017.01)
(Continued)

(52) U.S. Cl.
CPC ............ *G06T 7/0012* (2013.01); *A61B 6/032* (2013.01); *A61B 6/504* (2013.01); *A61B 6/5217* (2013.01);
(Continued)

(58) Field of Classification Search
CPC .............. G06T 7/0012; G06T 7/70; G06T 2207/10081; G06T 2207/10116;
(Continued)

(56) References Cited

U.S. PATENT DOCUMENTS

| | | |
|---|---|---|
| 8,238,635 B2 | 8/2012 | Can et al. |
| 9,165,362 B2 | 10/2015 | Siewerdsen et al. |
| 2020/0085393 A1* | 3/2020 | Zhang ............... A61B 6/54 |

OTHER PUBLICATIONS

Khaled Younis, et al., "Leveraging Deep Learning for Orientation Detection and Correction of X-Ray Images", Conference Paper, Aug. 2020, Conference on Machine Intelligence in Medical Imaging, SIIMU Online Learning, 6 pages.
(Continued)

*Primary Examiner* — Siamak Harandi
(74) *Attorney, Agent, or Firm* — Edell, Shapiro & Finnan, LLC

(57) ABSTRACT

A computer system identifies a medical condition in a patient. A trained machine learning image generator is used to generate a set of training images based on three-dimensional patient imaging data, wherein each training image is labeled with a projection angle of the corresponding two-dimensional projection. Using the set of training images, a machine learning image classifier model is trained to identify patient rotation angles in x-ray images. X-ray images are processed with the machine learning image classifier model to identify patient rotation angles. A machine learning medical condition classifier model is trained to identify a medical condition using the labeled x-ray images. The machine learning medical condition classifier model determines an indication of the medical condition in a patient's x-ray image. Embodiments of the present invention further include a method and program product for identifying a medical condition in a patient in substantially the same manner described above.

20 Claims, 8 Drawing Sheets

(51) Int. Cl.
  *G06N 3/04*    (2023.01)
  *A61B 6/00*    (2006.01)
  *A61B 6/03*    (2006.01)

(52) U.S. Cl.
  CPC ............. *G06N 3/04* (2013.01); *G06T 7/70* (2017.01); *G06T 2207/10081* (2013.01); *G06T 2207/10116* (2013.01); *G06T 2207/20081* (2013.01); *G06T 2207/20084* (2013.01); *G06T 2207/30101* (2013.01); *G06T 2207/30196* (2013.01)

(58) Field of Classification Search
  CPC . G06T 2207/20081; G06T 2207/20084; G06T 2207/30101; G06T 2207/30196; A61B 6/032; A61B 6/504; A61B 6/5217; A61B 6/503; G06N 3/04; G06N 3/045
  See application file for complete search history.

(56) References Cited

OTHER PUBLICATIONS

Hanming Zhang, et al., "Image Prediction for Limited-angle Tomography via Deep Learning with Convolutional Neural Network", arXiv preprint arXiv:1607.08707, Jul. 29, 2016, 21 pages.
Daniel Saez, "Correcting Image Orientation Using Convolutional Neural Networks", Jan. 12, 2017, https://d4nst.github.io/2017/01/12/image-orientation/, 37 pages.
Spyros Gidaris, et al., "Unsipervised Representation Learning by Predicting Image Rotations", Conference Paper, ICLR 2018, arXiv preprint arXiv:1803.07728, Mar. 21, 2018, 16 pages.
Yu-Xing Tang, et al., "Automated abnormality classification of chest radiographs using deep convolutional neural networks", NPJ digital medicine, May 14, 2020;3(1):1-8., 8 pages.
K.C. Santosh, et al., "Automatically detecting rotation in chest radiographs using principal rib-orientation measure for quality control", International Journal of Pattern Recognition and Artificial Intelligence, Mar. 8, 2015;29(02):1557001, 19 pages.
Ju Gang Nam, et al., "Development and validation of a deep learning algorithm detecting 10 common abnormalities on chest radiographs", European Respiratory Journal, May 1, 2021;57(5), 12 pages.

* cited by examiner

CLASSIFICATION OF MEDICAL IMAGES USING MACHINE LEARNING TO ACCOUNT FOR BODY ORIENTATION

BACKGROUND

1. Technical Field

Present invention embodiments relate to medical imaging and machine learning, and more specifically, to classifying medical images by performing machine learning in a manner that accounts for a patient's body orientation during imaging.

2. Discussion of the Related Art

In the field of medical imaging, health conditions are regularly identified based on images obtained via x-ray, medical resonance imaging, and computed tomography techniques. For example, thoracic aortic aneurysms can be diagnosed by identifying a potential widening of the mediastinum in an x-ray image and confirming with a follow-up computed tomography scan. However, distinguishing true abnormalities from false positives can be difficult if a patient is not imaged properly. For example, if a patient is rotated relative to an x-ray machine or is otherwise improperly positioned, the resulting x-ray images can give a false impression that the patient's mediastinum is widened.

SUMMARY

According to one embodiment of the present invention, a computer system identifies a medical condition in a patient. A trained machine learning image generator is used to generate a set of training images, wherein the set of training images is generated based on three-dimensional imaging data from a plurality of patients, wherein each training image is based on a two-dimensional projection of the three-dimensional imaging data of a particular patient, and wherein each training image is labeled with a projection angle of the corresponding two-dimensional projection. Using the set of training images, a machine learning image classifier model is trained to identify patient rotation angles in x-ray images. A set of x-ray images is processed with the machine learning image classifier model to identify a patient rotation angle for each x-ray image, wherein each x-ray image is labeled with a disease state. A machine learning medical condition classifier model is trained to identify a medical condition, wherein the machine learning medical condition classifier model is trained using the set of x-ray images labeled with the medical condition state and the patient rotation angle determined by the image classifier model. The machine learning medical condition classifier model is applied to determine an indication of the medical condition in an input x-ray image acquired from a patient. Embodiments of the present invention further include a method and program product for identifying a medical condition in a patient in substantially the same manner described above.

BRIEF DESCRIPTION OF THE DRAWINGS

Generally, like reference numerals in the various figures are utilized to designate like components.

DETAILED DESCRIPTION

Figure 1:
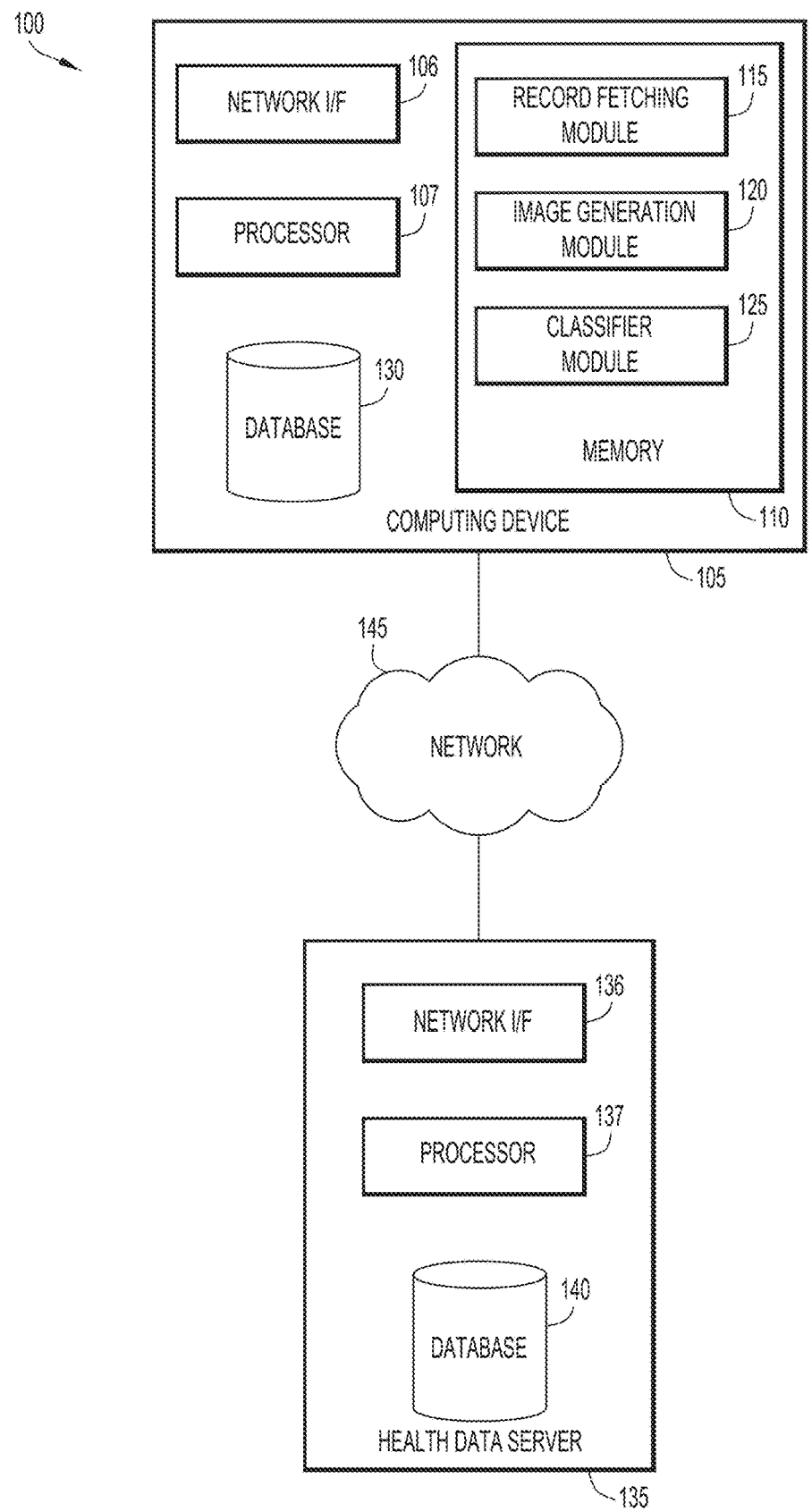
FIG. 1 is a block diagram depicting a computing environment for training and applying machine learning models to process medical images in accordance with an embodiment of the present invention.

Present invention embodiments relate to medical imaging and machine learning, and more specifically, to classifying medical images by applying machine learning in a manner that accounts for a patient's body orientation during imaging. Improper patient positioning during imaging can cause false positive diagnoses of certain medical conditions, such as thoracic aortic aneurysms. For example, the presence of a widened mediastinum, which is a compartment that runs the length of the thoracic cavity between the pleural sacs of the lungs, can be potentially indicative of a thoracic aortic aneurysm. However, if a patient is not properly aligned with an x-ray machine, the resulting medical images may give the appearance of a widened mediastinum despite no actual widening.

Similarly, confusion over the type of image being analyzed can lead to misdiagnoses. In particular, two types of x-ray images are posterior-anterior projections (in which the patient's posterior faces the x-ray source and anterior faces the detector), and anterior-posterior projections (in which the patient's anterior faces the x-ray source and posterior faces the detector). Due to the manner in which x-ray image projections are acquired, one cannot easily distinguish an anterior-posterior (AP) projection from a posterior-anterior (PA) projection, and accordingly, images are often labeled. When unlabeled, such images are often assumed to be a standard PA view; however, the mediastinum will appear larger in the AP view, so assuming that an unlabeled image is a PA view can lead to a misdiagnosis of a widened mediastinum.

Accordingly, present invention embodiments utilize machine learning techniques to train an image classifier to identify medical conditions based on patient images in a manner that detects and corrects for issues with a patient's body orientation during imaging. Conventional approaches struggle to account for unexpected AP views or a patient being imaged at an off-center angle, leading to false positives. Since conditions like thoracic aortic aneurysms are diagnosed by first performing an x-ray, and if the x-ray indicates that there may be an aneurysm, following up with a computed tomography (CT) scan to confirm, any false positives can lead to unnecessary CT scans. Thus, present invention embodiments reduce the number of false positives, which reduces the need for unnecessary CT scans, which can be costly, burdensome to the health care provider, and unhealthy to the patient, as CT scans involve a much greater dose of ionizing radiation as compared to x-rays.

Additionally, present invention embodiments utilize machine learning methods to generate training data for training the image classifier. Image generation models, such as generative adversarial networks (GANs), can be employed to generate artificial x-ray images from three-dimensional CT data. Thus, present invention embodiments provide the practical application of creating training data, which is extremely useful as the acquisition of accurate, representative training data is a long-standing problem in machine learning due to cost, time, and privacy concerns. Additionally, the image generation model(s) can perform other useful tasks, such as generating de-rotated x-ray images and/or converting PA images to AP images (and vice versa).

Thus, the embodiments presented herein improve machine learning and medical imaging by employing multiple machine learning models in tandem to provide a trained classifier that is much more accurate (e.g., producing fewer false positives) than conventional techniques. Additionally, the classifier can be trained using multi-task learning, thus ensuring that the classifier is accurate for images acquired at any body orientation, including both rotated orientations and non-rotated orientations. Thus, present invention embodiments improve the technical field of machine learning as applied to medical imaging in a manner that has the practical application of reducing the number of false positives, and accordingly, reducing the number of unnecessary CT scans that are performed.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Present invention embodiments will now be described in detail with reference to the Figures. FIG. 1 is a block diagram depicting a computing environment 100 for training and applying machine learning models to process medical images in accordance with an embodiment of the present invention. As depicted, computing environment 100 includes a computing device 105, a health data server 135, and a network 145. It is to be understood that the functional division among components of computing environment 100 have been chosen for purposes of explaining present invention embodiments and is not to be construed as a limiting example.

Computing device 105 includes a network interface (I/F) 106, at least one processor 107, memory 110, and a database 130. Memory 110 includes a record fetching module 115, an image generation module 120, and a classifier module 125. Computing device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of computing device 105 to send and receive data over a network, such as network 145. In general, computing device 105 performs machine learning tasks, including training machine learning models, acquiring or generating training data, and/or applying trained models to process medical images in accordance with present embodiments. Computing device 105 may include internal and external hardware components, as depicted and described in further detail with respect to FIG. 8.

Record fetching module 115, image generation module 120, and classifier module 125 may include one or more modules or units to perform various functions of present invention embodiments described below. Record fetching module 115, image generation module 120, and classifier module 125 may be implemented by any combination of any quantity of software and/or hardware modules or units, and may reside within memory 110 of computing device 105 for execution by a processor, such as processor 107.

Record fetching module 115 may obtain electronic health records, including medical images and other data, to support tasks in accordance with present invention embodiments. In some embodiments, record fetching module 115 accesses one or more databases, such as database 140 of health data server 135, to obtain electronic health records. The electronic health records may be used for training machine learning models, diagnosing medical conditions, and/or other purposes. In some embodiments, the electronic health records include medical images, including two-dimensional image data (e.g., x-rays, two-dimensional projections from three-dimensional CT data) and/or three-dimensional image data (e.g., CT data). Additionally or alternatively, the medical images may include MRI data, ultrasound data, positron-emission tomography data, and the like. Structured or unstructured health data may be associated with the medical images, such as diagnostic codes (e.g., International Statistical Classification of Diseases and Related Health Problems, $10^{th}$ revision (ICD-10) codes), or free-from text describing medical conditions or other aspects of a patient. The data obtained by record fetching module 115 may include unpaired medical images (e.g., medical images from different patients) and/or paired medical images (e.g., medical images from a same patient, such as a chest x-ray and CT scan of a same patient).

Image generation module 120 may generate, modify, transform, or otherwise process data, including medical image data, using machine learning techniques. In some embodiments, image generation module 120 extracts two-dimensional projections from three-dimensional CT data. The two-dimensional projections can correspond to any anatomical plane, such as sagittal or transverse, and may be tilted or rotated at any angle. In some embodiments, the two-dimensional projections can include maximum intensity projections (MIPs) and/or minimum intensity projections (MiniIPs).

In some embodiments, image generation module 120 uses machine learning techniques to train and apply image generation models. Image generation module 120 may train and/or apply one or more generative adversarial networks. A generative adversarial network (GAN) includes a generator, which learns to generate images, and a discriminator, which attempts to distinguish generated images from real images; when the discriminator can no longer tell the difference beyond a threshold level of accuracy, the training of the GAN may be completed. In various embodiments, image generation module 120 includes one or more machine learning models that can perform tasks including generating artificial x-ray images using three-dimensional CT data, de-rotating rotated x-ray images (e.g., converting an x-ray image taken at an angle to a plane, such as a coronal plane, into an x-ray image taken substantially orthogonal to the plane), and/or converting PA images to AP images or converting AP images into PA images.

In some embodiments, image generation module 120 includes a cycle GAN, which includes two GANs (and therefore, two generators and two discriminators). A cycle GAN can use unpaired training data to learn how to translate data from one domain to another without the need for one-to-one mappings between source and target domains. In some embodiments, a cycle GAN may be trained using unpaired images of x-rays and two-dimensional projections obtained from CT data to convert input two-dimensional projections from CT data into artificial x-ray images. Thus, image generation module 120 can generate artificial x-ray images using three-dimensional CT data, enabling image generation module 120 to create artificial x-ray images that correspond to any anatomical plane of a patient, including rotated planes.

Classifier module 125 may train and/or apply one or more machine learning models to classify medical conditions based on input medical images (e.g., x-ray images, CT data, etc.). In some embodiments, classifier module 125 employs an artificial neural network, such as a convolutional neural network, that is trained to classify medical conditions using training data that includes medical images labeled with a medical condition state. In particular, classifier module 125 may train and/or apply a machine learning model to determine whether x-ray images indicate the presence of a thoracic aortic aneurysm. In various embodiments, classifier module 125 may classify images for the presence of a thoracic aortic aneurysm by training a model to identify mediastinal widening, aortic enlargement, and/or aortic tortuosity. For example, a convolutional neural network can be trained to identify widening of the mediastinum using a set of training images of chest x-rays that are labeled with respect to the presence or absence of a widened mediastinum.

In some embodiments, classifier module 125 performs multi-task learning to train a machine learning model that achieves a desired threshold of classification accuracy for a variety of different x-ray rotation angles. Classifier module 125 may be provided with x-ray image sets for different angles of rotation, such as 0° to 5° from the orthogonal (e.g., orthogonal to a patient's coronal plane), 5° to 10° from the orthogonal, 10° to 15° from the orthogonal, and the like. Classifier module 125 may perform multi-task training by modifying the loss function such that accuracy is maintained for each range of angles; the resulting model can thus identify an angle of rotation of an x-ray image based on the image alone, and can determine whether the x-ray image indicates the presence of a medical condition (e.g., mediastinal widening).

Database 130 may include any non-volatile storage media known in the art. For example, database 130 can be implemented with a tape library, optical library, one or more independent hard disk drives, or multiple hard disk drives in a redundant array of independent disks (RAID). Similarly, data in database 130 may conform to any suitable storage architecture known in the art, such as a file, a relational database, an object-oriented database, and/or one or more tables. In some embodiments, database 130 may store data including trained machine learning models, training data, medical image data (e.g., x-ray data, CT data), two-dimensional projections obtained from CT data, artificial x-ray images generated by image generation module 120, and/or other images generated by image generation module 120.

Health data server 135 includes a network interface (I/F) 136, at least one processor 137, and a database 140. Health data server 135 may include a laptop computer, a tablet computer, a netbook computer, a personal computer (PC), a desktop computer, a personal digital assistant (PDA), a smart phone, a thin client, a rack-mounted server, or any programmable electronic device capable of executing computer readable program instructions. Network interface 136 enables components of health data server 135 to send and receive data over a network, such as network 145. In general, health data server 135 may store electronic health records, including medical images, and/or health record data, including structured and/or unstructured data). Health data server 135 may store the data in database 140, and may respond to requests for data by providing the requested data to the requesting entity (e.g., record fetching module 115 of computing device 105). Health data server 135 may include internal and external hardware components, as depicted and described in further detail with respect to FIG. 8.

Database 140 may include any non-volatile storage media known in the art. For example, database 140 can be implemented with a tape library, optical library, one or more independent hard disk drives, or multiple hard disk drives in a redundant array of independent disks (RAID). Similarly, data in database 140 may conform to any suitable storage architecture known in the art, such as a file, a relational database, an object-oriented database, and/or one or more tables. In some embodiments, database 140 may store data including electronic health records, such as medical images and corresponding diagnostic codes or diagnoses.

Network 145 may include a local area network (LAN), a wide area network (WAN) such as the Internet, or a combination of the two, and includes wired, wireless, or fiber optic connections. In general, network 145 can be any combination of connections and protocols known in the art that will support communications between computing device 105 and health data server 135 via their respective network interfaces in accordance with embodiments of the present invention.

Figure 2A:
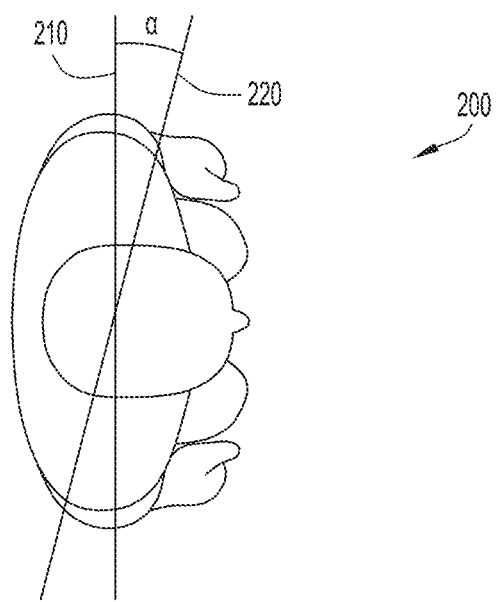
FIGS. 2A and 2B are diagrams depicting a patient being imaged in accordance with an embodiment of the present invention.
Figure 2B:
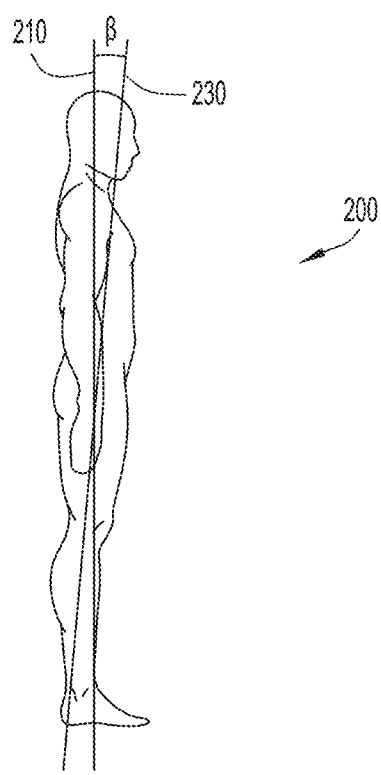

FIGS. 2A and 2B are diagrams depicting a patient 200 being imaged in accordance with an embodiment of the present invention.

FIG. 2A illustrates a top view of patient 200 and includes a coronal plane 210. Also included is a rotated plane 220, that is offset from coronal plane 210 by an angle α. Similarly, FIG. 2B illustrates a side view of patient 200 and includes coronal plane 210 and another rotated plane 230 that is offset from coronal plane 210 by an angle β. As used herein, a rotated plane or rotated image refers to an image acquired by an imaging device being that is positioned orthogonal to a rotated plane, such as plane 220 or 230. It should be appreciated that a medical image can be rotated in any direction from any plane, including coronal plane 210 as well as a transverse or sagittal plane.

Figure 3:
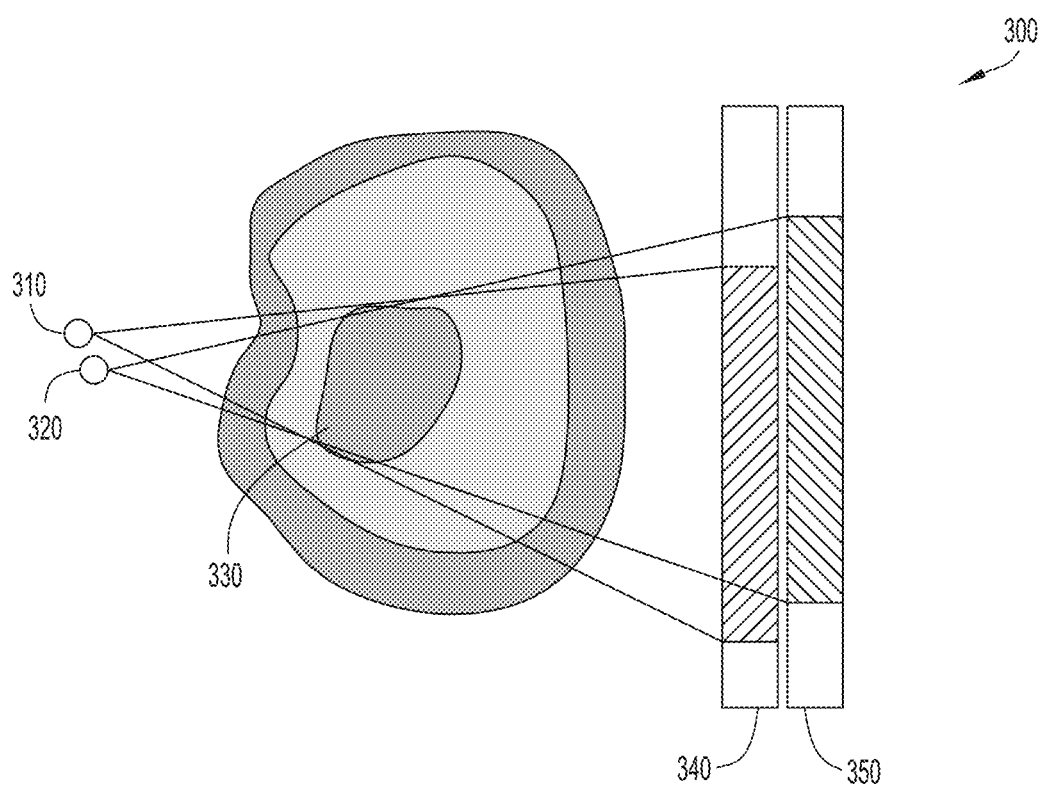
FIG. 3 depicts a transverse plane of a patient being imaged in accordance with an embodiment of the present invention.

FIG. 3 depicts a transverse plane 300 of a patient being imaged in accordance with an embodiment of the present invention. As shown, an x-ray image is acquired from two different x-ray source locations, 310 and 320. Also depicted is an anatomical feature 330 and x-ray detectors 340 and 350. The x-ray emissions are depicted as overlapping in FIG. 3 for the purpose of illustrating how different x-ray source locations can cause differences in the appearance of anatomical features in the resulting x-ray images.

As shown, x-ray source 320 may correspond to an x-ray acquired from a location orthogonal to a coronal plane of a patient and centered on the patient. In contrast, x-ray source 310 is offset, causing the resulting x-ray image to be rotated. Due to the different location of the x-ray sources, anatomical feature 330 is projected differently onto x-ray detectors 340 and 350, causing anatomical feature 330 to have two different sizes.

Figure 4A:
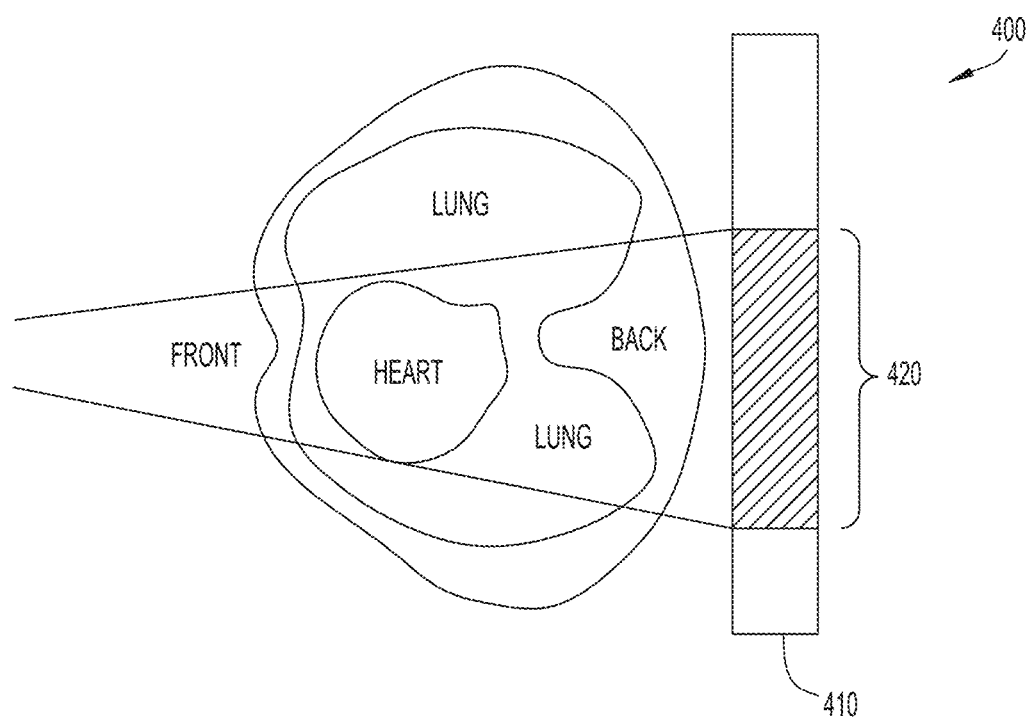
FIGS. 4A and 4B depict transverse planes of a patient being imaged in accordance with an embodiment of the present invention.
Figure 4B:
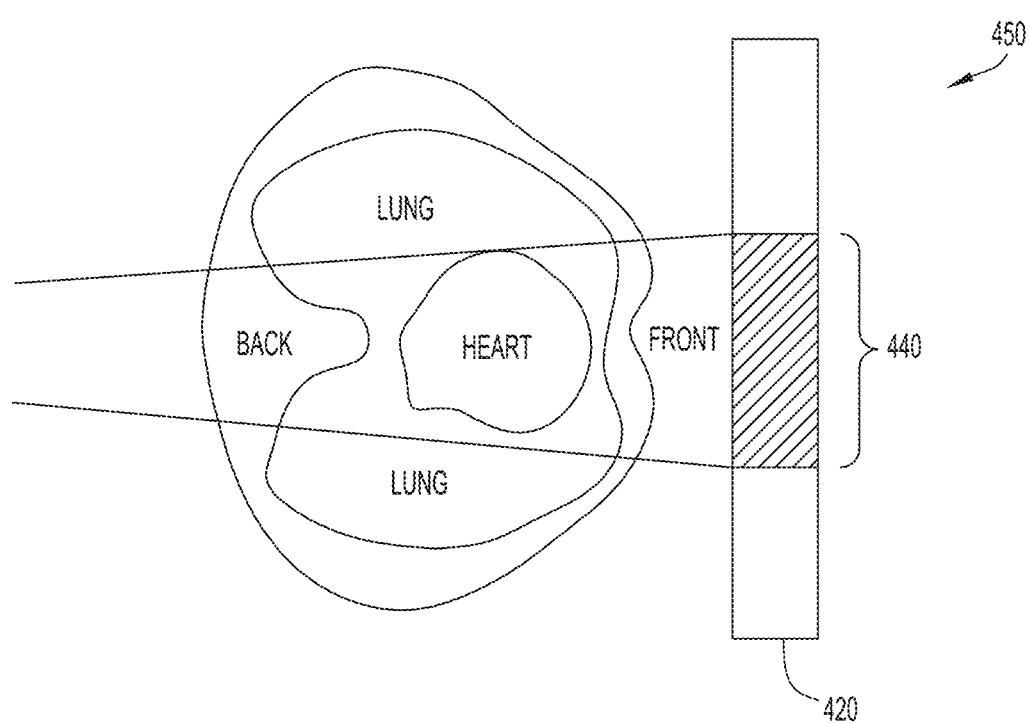

FIGS. 4A and 4B depict transverse planes 400 and 450 of a patient being imaged in accordance with an embodiment of the present invention.

As shown in FIG. 4A, the transverse plane 400 depicts an AP projection is being acquired by x-ray detector 410; the width of the patient's heart is represented as projection 420. The x-rays pass from the anterior of the patient and exit through the posterior before being detected by x-ray detector 410.

In contrast, FIG. 4B depicts an embodiment in which transverse plane 450 is shown with a PA projection being acquired by x-ray detector 420; the width of the patient's heart is represented as projection 440. Because the patient's heart is farther from the x-ray source, and closer to x-ray detector 420, a PA projection has a smaller projection 440 of the heart as compared to an AP projection (e.g., projection 420).

Figure 5:
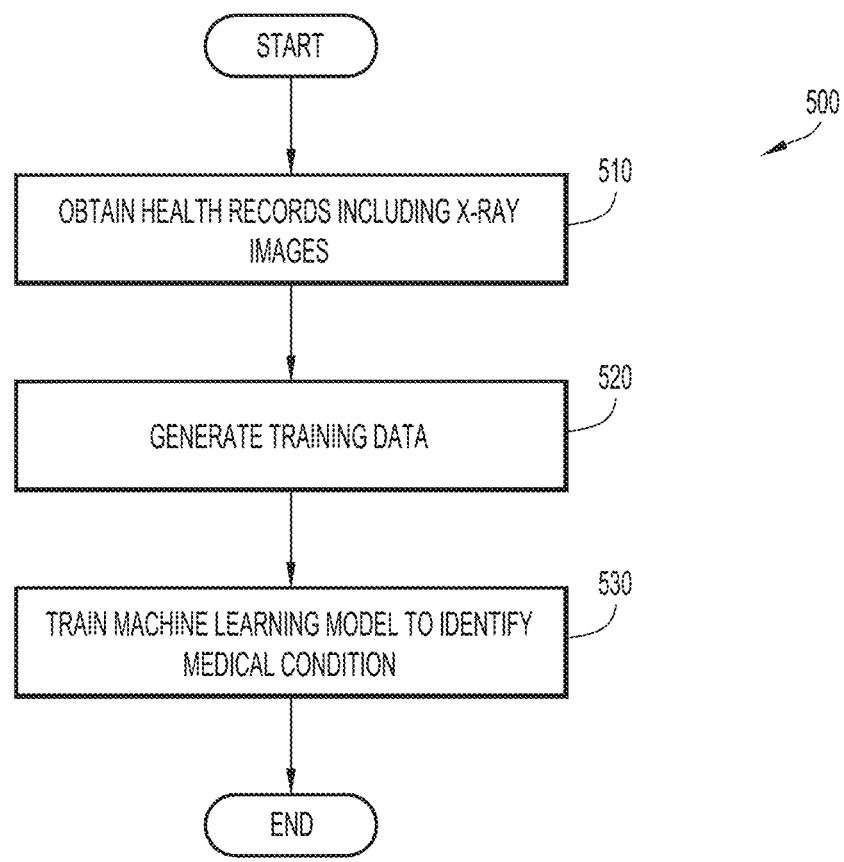
FIG. 5 is a flow chart depicting a method of training a medical condition classifier model using machine learning in accordance with an embodiment of the present invention.

FIG. 5 is a flow chart depicting a method 500 of training a medical condition classifier model using machine learning in accordance with an embodiment of the present invention.

Health records including x-ray images are obtained at operation 510. The health records may be obtained from one or more locations, including local storage locations (e.g., database 130 of computing device 105) and/or network-accessible locations (e.g., database 140 of health data server 135). The health records may include x-ray images, such as chest x-ray images, of patients, as well as data describing the patient, such as a diagnosis or other details regarding a patient.

Training data is generated at operation 520. Classifier module 125 may generate a set of training data by processing the health records to extract x-ray images, and labeling each x-ray image with respect to the presence or absence of a medical condition. For example, chest x-ray images may be labeled as either indicating a widened mediastinum or not indicating a widened mediastinum. In various embodiments, the medical condition may include a widened mediastinum, aortic enlargement, aortic tortuosity, and/or any other medical condition that can be observed. In some embodiments, the labels for x-ray images are determined according to patient medical records associated with the x-ray images. The medical records may be structured and/or unstructured. For structured records, a predefined field may indicate the presence or absence of a medical condition. For unstructured records, such as free-form text written by a health care provider, classifier module 125 may employ conventional or other natural language processing techniques in order to extract an indication of the presence or absence of a medical condition.

A machine learning model is trained to identify a medical condition at operation 530. Classifier module 125 may train a neural network, such as a convolutional neural network, to classify x-ray images for the presence or absence of a medical condition. The medical condition classifier model may be trained, using the set of training data generated by classifier module 125, until a desired level of accuracy is achieved. Once trained, the medical condition classifier model can be applied to classification tasks, such as identifying an indication of a widened mediastinum in x-ray images. The trained medical condition classifier model may be re-trained using additional training data in accordance with present invention embodiments in order to support classification of x-ray images taken at a variety of rotations.

Figure 6:
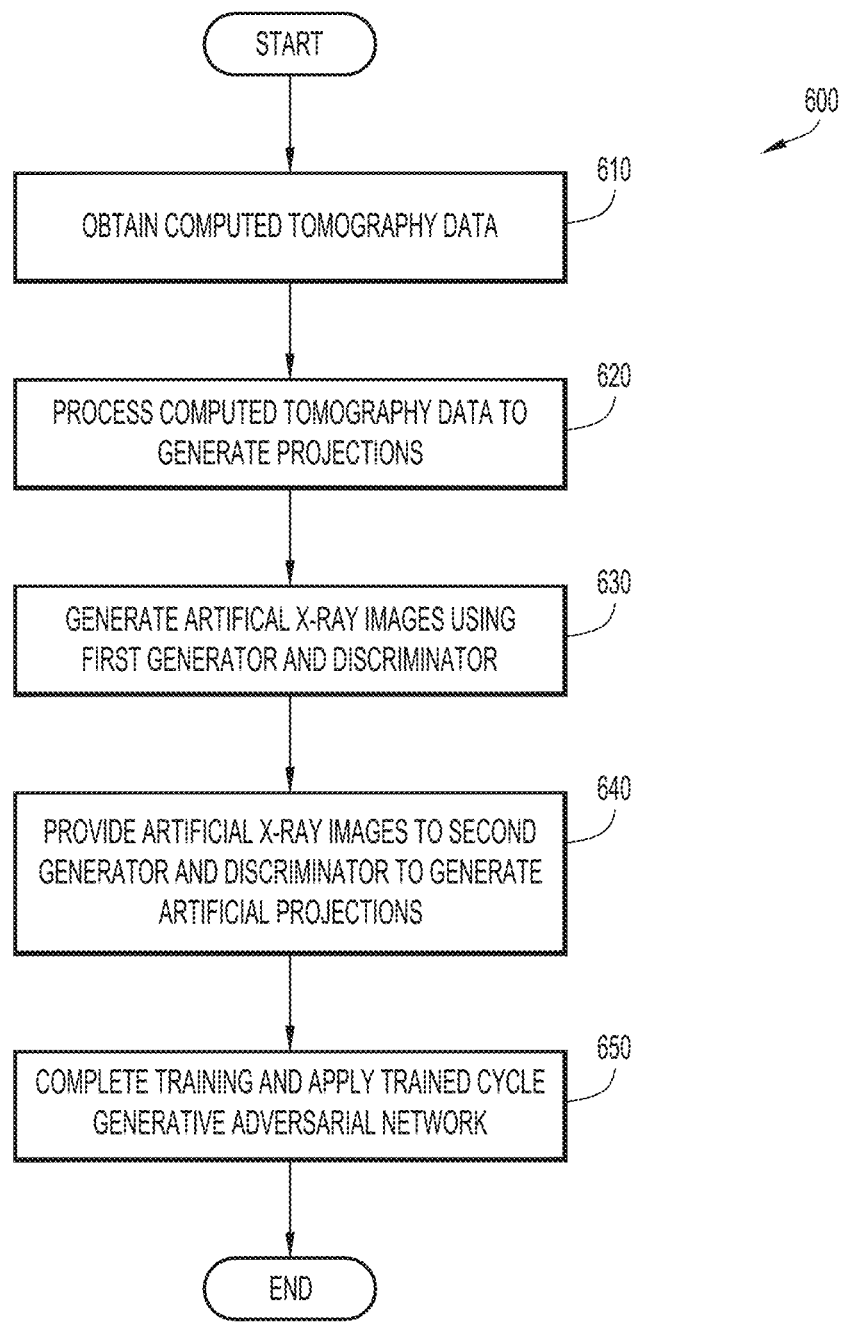
FIG. 6 is a flow chart depicting a method of training an image generator using machine learning in accordance with an embodiment of the present invention.

FIG. 6 is a flow chart depicting a method 600 of training an image generator using machine learning in accordance with an embodiment of the present invention.

Computed tomography (CT) data is obtained at operation 610. Image generation module 120 may obtain CT data from one or more locations, including local storage locations (e.g., database 130 of computing device 105) and/or network-accessible locations (e.g., database 140 of health data server 135). The CT data may be three-dimensional data that can be converted to two-dimensional projections (e.g., maximum intensity projections). The two-dimensional projections can be obtained for any desired two-dimensional plane passing through an imaged subject. The CT data may include data from multiple patients, and can be representative of a variety of body shapes and sizes, as well as medical conditions.

The CT data is processed to generate projections at operation 620. Two-dimensional projections may be taken by extracting a plane of the three-dimensional CT data. Multiple two-dimensional projections may be extracted from each patient's CT data. Two-dimensional projections may be extracted by varying angles of the plane to mimic the effect of a rotated x-ray; for example, with reference to FIGS. 2A and 2B, angles α and β, as well as additional angles, may be incrementally adjusted to acquire a set of images from the CT data that are similar in perspective to rotated x-ray images. Subsets of images for ranges of rotational angles may be acquired for later use in multi-task training of a medical condition classifier model; for example, multiple images may be obtained, from multiple patient's CT data, for ranges of angles such as 0° to 5°, 5° to 10°, 10° to 15°, and the like. Any granularity of ranges for the subset of images may be selected.

Artificial x-ray images are generated using a first generator and discriminator at operation 630. A first GAN that includes a first generator-discriminator pair may be trained to generate artificial x-ray images using the extracted two-dimensional projections and examples of x-rays as training data. The examples of x-rays do not need to correspond to the same patient from whom the two dimensional projections are obtained (as the first GAN can be paired with a second GAN to provide a cycle GAN that does not require paired data for training). The first discriminator may estimate whether images generated by the first generator are true x-ray images or artificial x-ray images, and when the first discriminator can no longer accurately estimate the difference between true and artificial x-ray images (e.g., beyond a threshold level of accuracy), training may be completed for the first GAN.

The artificial x-ray images are provided to a second generator and discriminator to generate artificial projections at operation 640. During training of the first GAN, a second GAN, including a second generator and discriminator, may be trained to perform the reverse process of the first GAN (e.g., converting artificial x-ray images back into artificial two-dimensional projections of CT data). A cycle GAN can be developed by linking the first GAN and second GAN during training, with the second GAN's output images (the artificial two-dimensional projections) being compared to the actual two-dimensional projections provided as input to the first GAN to determine how similar the artificial two-dimensional projections are to the original two-dimensional projections.

Training is completed and the trained cycle GAN is applied to image generation tasks at operation 650. When the second discriminator can no longer accurately (e.g., beyond a threshold level of accuracy) differentiate between artificial two-dimensional projections and their counterpart original two-dimensional projections, training of the cycle GAN is complete. As a result, the trained image generator can convert CT data into realistic artificial x-ray images that capture the particular anatomy of the patient whose CT data was used to create two-dimensional projections. Additionally, the image generator can convert x-rays into two-dimensional projections. In various embodiments, GANs may be trained to support additional image generation tasks, such as generating rotated x-ray images from non-rotated x-ray images, generating de-rotated x-ray images from rotated x-ray images, generating AP x-ray images from PA x-ray images, generating PA x-ray images from AP x-ray images, and the like.

Figure 7:
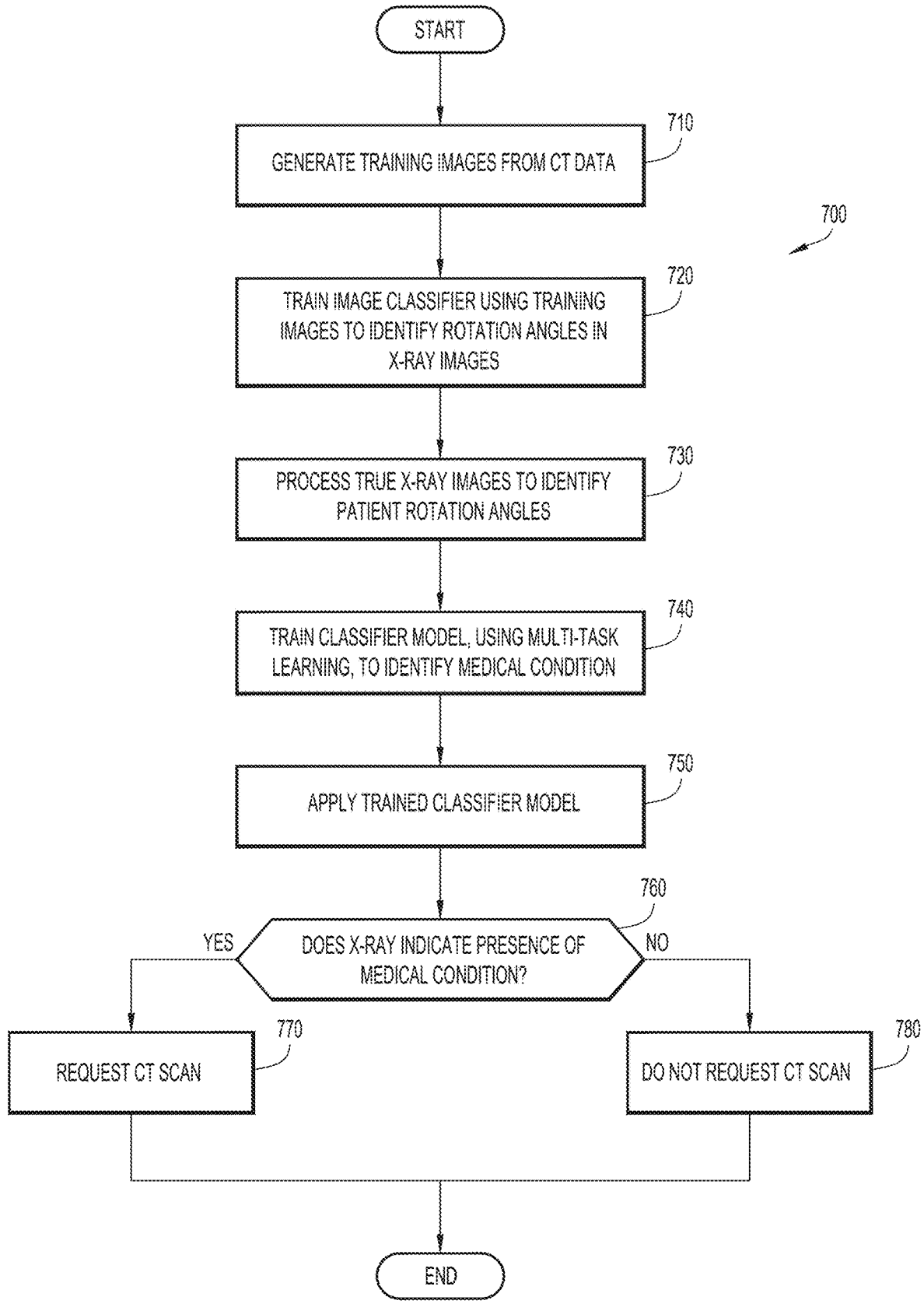
FIG. 7 is a flow chart depicting a method of training a medical condition classifier model in accordance with an embodiment of the present invention.

FIG. 7 is a flow chart depicting a method 700 of training a medical condition classifier model in accordance with an embodiment of the present invention.

Training images are generated from CT data at operation 710. A set of training images of artificial x-rays may be generated by image generation module 120 to obtain training images representative of any desired x-ray rotation angle. Since the artificial x-rays are generated based on three-dimensional CT data, any rotation angle can be obtained. The training data may include a sufficient number of example images for each rotation angle or range of angles into to ensure a high level of accuracy of the classifier model that will be trained using the artificial x-ray images.

An image classifier is trained using training images to identify rotation angles in x-ray images at operation 720. The classifier may include a neural network, such as a convolutional neural network. The classifier may be trained using the set of training data that includes artificial x-rays, which are labeled with their rotation angle. Once training is completed, the image classifier can be applied to determine a patient rotation angle by processing true x-ray images of patients.

A set of true x-ray images are processed to identify patient rotation angles at operation 730. The image classifier that is trained using artificial x-rays and known rotation angles can be applied to determine rotation angles for x-ray images. Each x-ray image may be labeled with its rotation angle to produce a new set of training data that includes true x-ray images and angles of rotation. Additionally, each x-ray image in the training data may be labeled with respect to a medical condition state.

A medical condition classifier model is trained, using multi-task learning, to identify one or more medical conditions at operation 740. The training data of x-ray images may be separated into subsets of images by rotation angle range (e.g., 0° to 5°, 5° to 10°, etc.). A classifier model may then be trained using multi-task learning, which tracks the accuracy of the classifier for detection of a medical condition for each range of angles, and adjusts the loss function accordingly until the classifier achieves a desired level of accuracy for each rotation angle range. The classifier that is trained using multi-task learning may be pre-trained, and may correspond to the classifier model trained according to the method 500, depicted and described with reference to FIG. 5. Multi-task training of the medical condition classifier may be completed when the classifier accurately classifies x-ray images for the presence or absence of a medical condition at a threshold level of accuracy for each range of patient rotation angles.

The trained classifier model is applied at operation 750. X-ray images of patients may be provided to the trained classifier model, which can then determine whether the x-ray images indicate the presence or absence of a particular medical condition (e.g., mediastinal widening, aortic enlargement, aortic tortuosity, etc.). In some embodiments, AP x-ray images are converted to PA x-ray images, or PA x-ray images are converted to AP x-ray images, prior to providing those images to the classifier model.

At operation 760, the trained classifier model determines whether an x-ray image indicates the presence of a medical condition. If an x-ray image indicates the presence of the medical condition, a notification may be provided to request a follow-up CT scan of the patient to confirm. If so, a CT scan is requested for the patient at operation 770. In some embodiments, computing device 105 may automatically initiate a CT scan by transmitting instructions to a CT machine or other medical device to initiate collection of CT data. Otherwise, a CT scan is not requested for the patient at operation 780. Accordingly, present invention embodiments improve the accuracy of medical diagnoses by enabling medical conditions to be more accurately identified regardless of any patient rotation angles in x-ray images.

Figure 8:
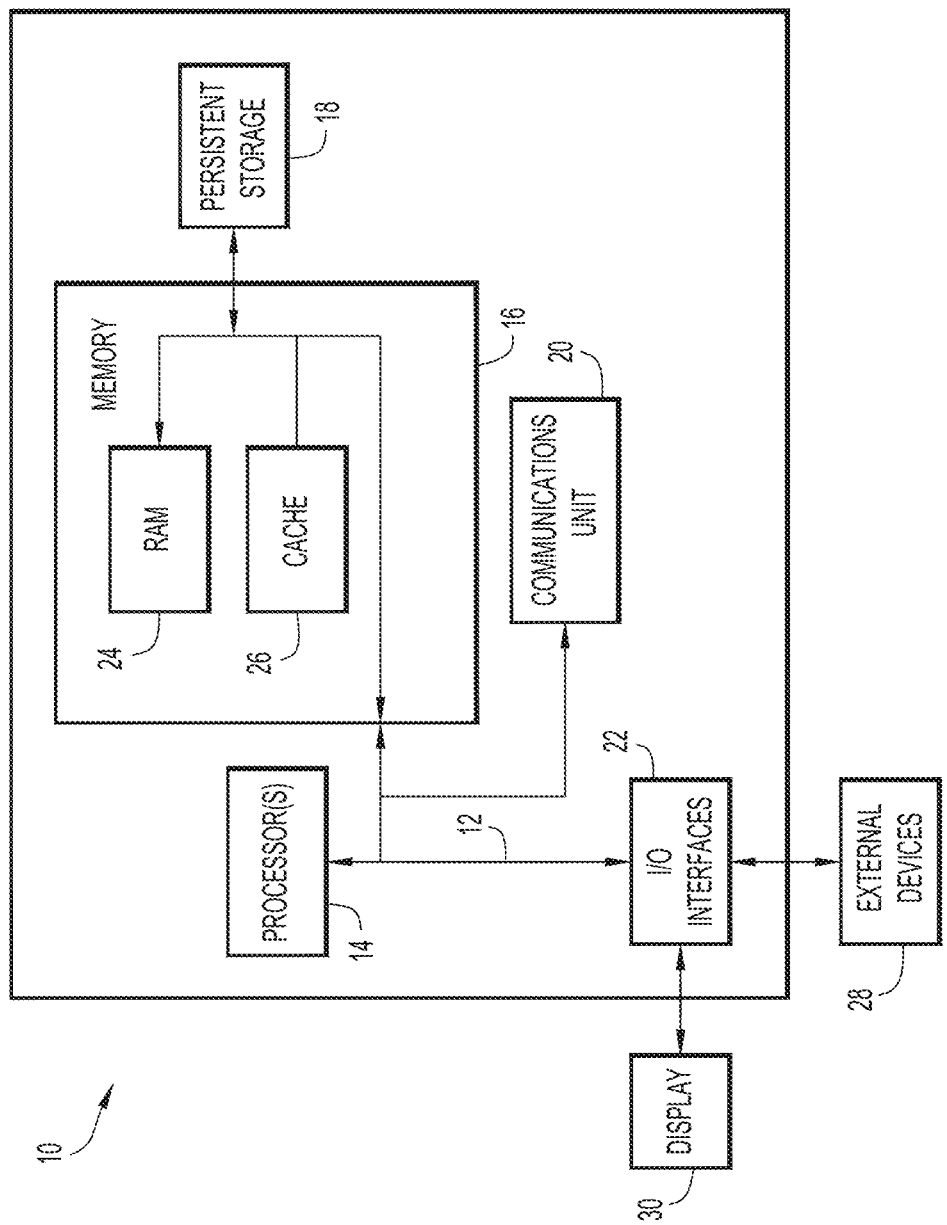
FIG. 8 is a block diagram depicting a computing device in accordance with an embodiment of the present invention.

FIG. 8 is a block diagram depicting components of a computer 10 suitable for executing the methods disclosed herein. Computer 10 may implement computing device 105 and/or health data server 135 in accordance with embodiments of the present invention. It should be appreciated that FIG. 8 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to identifying a medical condition in a patient (e.g., x-ray image data, CT data, generated image data, (e.g., AP images generated from PA images, PA images generated from AP images, de-rotated images generated from rotated images, artificial x-ray images generated from two-dimensional projections, artificial two-dimensional projections generated from artificial x-ray images, etc.), trained model data, training data, including artificial x-ray image training sets, two-dimensional projections, true x-ray image sets, etc.) may be stored within any conventional or other data structures (e.g., files, arrays, lists, stacks, queues, records, etc.) and may be stored in any desired storage unit (e.g., database, data or other repositories, queue, etc.). The data transmitted between computing device 105 and/or health data server 135 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to identifying a medical condition in a patient (e.g., x-ray image data, CT data, generated image data, (e.g., AP images generated from PA images, PA images generated from AP images, de-rotated images generated from rotated images, artificial x-ray images generated from two-dimensional projections, artificial two-dimensional projections generated from artificial x-ray images, etc.), trained model data, training data, including artificial x-ray image training sets, two-dimensional projections, true x-ray image sets, etc.) may include any information provided to, or generated by, computing device 105 and/or health data server 135. Data relating to identifying a medical condition in a patient may include any desired format and arrangement, and may include any quantity of any types of fields of any size to store any desired data. The data relating to identifying a medical condition in a patient may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to identifying a medical condition in a patient), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of improving medical condition identification via machine learning techniques.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., communications software, server software, record fetching module 115, image generation module 120, classifier module 125, etc.). These systems may include any types of monitors and input devices (e.g., keyboard, mouse, voice recognition, etc.) to enter and/or view information.

It is to be understood that the software (e.g., communications software, server software, record fetching module 115, image generation module 120, classifier module 125, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., communications software, server software, record fetching module 115, image generation module 120, classifier module 125, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to identifying a medical condition in a patient). The database system may be implemented by any number of any conventional or other databases, data stores or storage structures (e.g., files, databases, data structures, data or other repositories, etc.) to store information (e.g., data relating to identifying a medical condition in a patient). The database system may be included within or coupled to the server and/or client systems. The database systems and/or storage structures may be remote from or local to the computer or other processing systems, and may store any desired data (e.g., data relating to identifying a medical condition in a patient).

The present invention embodiments may employ any number of any type of user interface (e.g., Graphical User Interface (GUI), command-line, prompt, etc.) for obtaining or providing information (e.g., data relating to identifying a medical condition in a patient), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, providing improved identification of any observable medical condition in a patient.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for identifying a medical condition in a patient, the method comprising:
    generating, using a trained machine learning image generator, a set of training images, wherein the set of training images is generated based on three-dimensional imaging data from a plurality of patients, wherein each training image is based on a two-dimensional projection of the three-dimensional imaging data of a particular patient, and wherein each training image is labeled with a projection angle of the corresponding two-dimensional projection;
    training, using the set of training images, a machine learning image classifier model to identify patient rotation angles in x-ray images;
    processing a set of x-ray images with the machine learning image classifier model to identify a patient rotation angle for each x-ray image, wherein each x-ray image is labeled with a disease state;
    training a machine learning medical condition classifier model to identify a medical condition, wherein the machine learning medical condition classifier model is trained using the set of x-ray images labeled with the medical condition state and the patient rotation angle determined by the image classifier model; and
    applying the machine learning medical condition classifier model to determine an indication of the medical condition in an input x-ray image acquired from a patient.

2. The computer-implemented method of claim 1, further comprising:
applying the trained machine learning image generator to generate one or more of: an anterior-posterior x-ray projection image based on a posterior-anterior x-ray projection image, and an de-rotated x-ray image based on an x-ray image having a non-zero patient rotation angle.

3. The computer-implemented method of claim 1, wherein the medical condition includes one or more of: thoracic mediastinum widening, aortic enlargement, and tortuosity of a thoracic aorta.

4. The computer-implemented method of claim 1, wherein the machine learning medical condition classifier model is a pre-trained convolutional neural network, wherein training the machine learning medical condition classifier model comprises retraining the pre-trained convolutional neural network via multi-task learning, and wherein the set of x-ray images labeled with the medical condition state and the patient rotation angle are grouped into subsets of rotation angle ranges for the multi-task learning.

5. The computer-implemented method of claim 1, wherein the trained machine learning image generator includes a cycle generative adversarial network, and wherein the set of training images generated by the trained image generator includes synthetic x-ray images generated based on two-dimensional projections of the computed tomography data.

6. The computer-implemented method of claim 1, further comprising:
in response to determining the indication of the medical condition, transmitting an instruction to obtain computed tomography imagery from the patient to verify a presence of the medical condition.

7. The computer-implemented method of claim 1, wherein the two-dimensional projection is a maximum intensity projection.

8. A computer system for identifying a medical condition in a patient, the computer system comprising:
one or more computer processors;
one or more computer readable storage media;
program instructions stored on the one or more computer readable storage media for execution by at least one of the one or more computer processors, the program instructions comprising instructions to:
generate, using a trained machine learning image generator, a set of training images, wherein the set of training images is generated based on three-dimensional imaging data from a plurality of patients, wherein each training image is based on a two-dimensional projection of the three-dimensional imaging data of a particular patient, and wherein each training image is labeled with a projection angle of the corresponding two-dimensional projection;
train, using the set of training images, a machine learning image classifier model to identify patient rotation angles in x-ray images;
process a set of x-ray images with the machine learning image classifier model to identify a patient rotation angle for each x-ray image, wherein each x-ray image is labeled with a disease state;
train a machine learning medical condition classifier model to identify a medical condition, wherein the machine learning medical condition classifier model is trained using the set of x-ray images labeled with the medical condition state and the patient rotation angle determined by the image classifier model; and
apply the machine learning medical condition classifier model to determine an indication of the medical condition in an input x-ray image acquired from a patient.

9. The computer system of claim 8, wherein the program instructions further comprise instructions to:
apply the trained machine learning image generator to generate one or more of: an anterior-posterior x-ray projection image based on a posterior-anterior x-ray projection image, and an de-rotated x-ray image based on an x-ray image having a non-zero patient rotation angle.

10. The computer system of claim 8, wherein the medical condition includes one or more of: thoracic mediastinum widening, aortic enlargement, and tortuosity of a thoracic aorta.

11. The computer system of claim 8, wherein the machine learning medical condition classifier model is a pre-trained convolutional neural network, wherein training the machine learning medical condition classifier model comprises retraining the pre-trained convolutional neural network via multi-task learning, and wherein the set of x-ray images labeled with the medical condition state and the patient rotation angle are grouped into subsets of rotation angle ranges for the multi-task learning.

12. The computer system of claim 8, wherein the trained machine learning image generator includes a cycle generative adversarial network, and wherein the set of training images generated by the trained image generator includes synthetic x-ray images generated based on two-dimensional projections of the computed tomography data.

13. The computer system of claim 8, wherein the program instructions further comprise instructions to:
in response to determining the indication of the medical condition, transmit an instruction to obtain computed tomography imagery from the patient to verify a presence of the medical condition.

14. The computer system of claim 8, wherein the two-dimensional projection is a maximum intensity projection.

15. A computer program product for identifying a medical condition in a patient, the computer program product comprising one or more computer readable storage media collectively having program instructions embodied therewith, the program instructions executable by a computer to cause the computer to:
generate, using a trained machine learning image generator, a set of training images, wherein the set of training images is generated based on three-dimensional imaging data from a plurality of patients, wherein each training image is based on a two-dimensional projection of the three-dimensional imaging data of a particular patient, and wherein each training image is labeled with a projection angle of the corresponding two-dimensional projection;
train, using the set of training images, a machine learning image classifier model to identify patient rotation angles in x-ray images;
process a set of x-ray images with the machine learning image classifier model to identify a patient rotation angle for each x-ray image, wherein each x-ray image is labeled with a disease state;
train a machine learning medical condition classifier model to identify a medical condition, wherein the machine learning medical condition classifier model is trained using the set of x-ray images labeled with the medical condition state and the patient rotation angle determined by the image classifier model; and apply the machine learning medical condition classifier model to determine an indication of the medical condition in an input x-ray image acquired from a patient.

16. The computer program product of claim 15, wherein the program instructions further cause the computer to:
apply the trained machine learning image generator to generate one or more of: an anterior-posterior x-ray projection image based on a posterior-anterior x-ray projection image, and an de-rotated x-ray image based on an x-ray image having a non-zero patient rotation angle.

17. The computer program product of claim 15, wherein the medical condition includes one or more of: thoracic mediastinum widening, aortic enlargement, and tortuosity of a thoracic aorta.

18. The computer program product of claim 15, wherein the machine learning medical condition classifier model is a pre-trained convolutional neural network, wherein training the machine learning medical condition classifier model comprises retraining the pre-trained convolutional neural network via multi-task learning, and wherein the set of x-ray images labeled with the medical condition state and the patient rotation angle are grouped into subsets of rotation angle ranges for the multi-task learning.

19. The computer program product of claim 15, wherein the trained machine learning image generator includes a cycle generative adversarial network, and wherein the set of training images generated by the trained image generator includes synthetic x-ray images generated based on two-dimensional projections of the computed tomography data.

20. The computer program product of claim 15, wherein the program instructions further cause the computer to:
in response to determining the indication of the medical condition, transmit an instruction to obtain computed tomography imagery from the patient to verify a presence of the medical condition.

* * * * *